(12) United States Patent
Heacox

(10) Patent No.: US 8,609,120 B2
(45) Date of Patent: Dec. 17, 2013

(54) USE AND GENERATION OF OZONE AS A DISINFECTANT OF DAIRY ANIMAL TISSUES, DAIRY EQUIPMENT, AND INFRASTRUCTURE

(76) Inventor: Dana Heacox, Roswell, NM (US)

(*) Notice: Subject to any disclaimer, the term of this patent is extended or adjusted under 35 U.S.C. 154(b) by 0 days.

(21) Appl. No.: 13/183,826

(22) Filed: Jul. 15, 2011

(65) Prior Publication Data

US 2012/0015043 A1    Jan. 19, 2012

Related U.S. Application Data

(60) Provisional application No. 61/364,498, filed on Jul. 15, 2010.

(51) Int. Cl.
| | |
|---|---|
| *A01N 25/00* | (2006.01) |
| *A01N 59/00* | (2006.01) |
| *A61K 33/00* | (2006.01) |
| *A61K 51/00* | (2006.01) |
| *A61K 9/12* | (2006.01) |
| *A61M 36/14* | (2006.01) |

(52) U.S. Cl.
USPC ............. 424/405; 424/600; 424/1.13; 424/44

(58) Field of Classification Search
None
See application file for complete search history.

(56) References Cited

U.S. PATENT DOCUMENTS

| | | | |
|---|---|---|---|
| 5,098,415 A * | 3/1992 | Levin ........................... 604/293 |
| 2006/0124066 A1 | 6/2006 | Mitchell | |
| 2007/0163935 A1* | 7/2007 | Chewins ................... 210/198.1 |
| 2008/0223788 A1* | 9/2008 | Rimdzius et al. ............. 210/664 |
| 2010/0139723 A1 | 6/2010 | Torgerson et al. | |
| 2010/0154900 A1 | 6/2010 | Torgerson et al. | |

OTHER PUBLICATIONS

Ozone Solutions (Ambient Leak Detection, Wayback Machine, Sep. 6, 2007).*

* cited by examiner

*Primary Examiner* — Cherie M Stanfield
*Assistant Examiner* — Mark V Stevens
(74) *Attorney, Agent, or Firm* — Melissa Silverstein; Luis M. Ortiz; Kermit D. Lopez

(57) ABSTRACT

An ozone delivery system, method, and apparatus are disclosed. Ozonated water can be used to disinfect and clean various surfaces, equipment, and animals in a dairy setting. Animals can be disinfected and protected from disease through the use of wash-pen and sprayer injections, and other footbath products. Ozone can be educted into a drop hose and a pre-dip line at periodic intervals and into a foot bath to provide refreshed ozonated water. The ozone delivery system and method sterilizes all equipment and floor surfaces without damaging diary equipment components. The system can incorporate computer-controlled options such as maintaining off gas levels, maintaining cleaning and disinfecting records, monitoring ozonated water levels, monitoring concentrations of ozone in said ozonated water, controlling entry and exit gates, controlling a drainage system, and monitoring and educting ozone in a foot bath and wash pen.

20 Claims, 6 Drawing Sheets

USE AND GENERATION OF OZONE AS A DISINFECTANT OF DAIRY ANIMAL TISSUES, DAIRY EQUIPMENT, AND INFRASTRUCTURE

CROSS REFERENCE TO RELATED APPLICATIONS

This patent application claims the benefit under 35 U.S.C. §119(e) of U.S. Provisional Patent Application Ser. No. 61/364,498 filed on Jul. 15, 2010, and entitled "Ozone Delivery System and Method," which is hereby incorporated by reference in its entirety.

TECHNICAL HELD

The disclosed embodiments relate to dairy operations. The disclosed embodiments further relate to disinfecting dairy farm equipment. The disclosed embodiments also relate to using ozonated water to safely disinfect animals and equipment.

BACKGROUND OF THE INVENTION

With increased globalization of agricultural markets, greater demands are placed on producers of milk and milk products. Milk is produced as inexpensively as possible while conforming to high quality standards. Large quantities of milk are produced in automatic or semiautomatic milking plants.

Dairy milking systems can include a cluster of teat cups matched with flexible teat cup liners. The teat cups are attached to a teat of a dairy animal with a vacuum to facilitate movement of the flexible liner to milk the dairy animals. Milk flows from the dairy animal through each flexible liner and then through a short milk tube to a milker unit collecting bowl assembly, which collects milk from all of the animal's teats. Milk from individual animals flow from each collecting bowl assembly through a long milk tube and into a milk line that receives milk from all of the milker units in the dairy. The milk is then chilled and stored in a milk tank. The milk lines and storage systems must not be contaminated with dirt, debris, chemicals, pathogens, or contaminated milk. This milker unit can be used to milk cows, sheep, goats, and other dairy animals. Each milker unit can be used to milk multiple animals, thus necessitating sanitization measures to prevent transmission of dirt and bacteria into the milk and diseases transmitted between animals.

A dairy's somatic cell count (i.e., "SCC") is the bacteria count in the final milk product. SCC levels are monitored to comply with state and federal milk quality standards. To avoid elevated SCC levels, dairies take disinfecting measures such as a teat pre-dip, for example. Broadened milk ducts in dairy animals' teats make the teats especially susceptible to infection from mastitis pathogens. The teats can be treated with a disinfectant solution, its application process known as pre-dipping. Prior automatic teat dip applicators and milker unit cleaner systems fail to adequately ensure that teat dip compositions and backflushing fluids do not enter the long milk tube and contaminate the dairy milk lines. Differential pressures between the milk lines, dipping, and backflushing devices can cause seepage into the milking system.

Accordingly, there exists a need for an improved ozone delivery system that uses ozonated water to safely disinfect dairy animal tissues, dairy equipment, and infrastructure, and reduce the need for harmful chemical disinfectants around a dairy.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is therefore an object of the disclosed embodiments to provide an improved disinfecting and cleaning system.

It is another object of the disclosed embodiments to disinfect animals and prevent disease.

It is an additional object of the disclosed embodiments to provide ozonated water to disinfect animals, equipment, and surfaces.

The above and other aspects can be achieved as is now described. An ozone delivery system, method, and apparatus are disclosed. Ozonated water can be used to disinfect and clean various surfaces, equipment, and animals in a dairy setting. Animals can be disinfected and protected from disease through the use of wash-pen and sprayer injections, and other footbath products. Ozone can be educted into a drop hose and a pre-dip line at periodic intervals and into a foot bath to provide refreshed ozonated water. The ozone delivery system and method sterilizes all equipment and floor surfaces without damaging diary equipment components. The system can incorporate computer-controlled options such as maintaining off gas levels, maintaining cleaning and disinfecting records, monitoring ozonated water levels, monitoring concentrations of ozone in said ozonated water, controlling entry and exit gates, controlling a drainage system, and monitoring and educting ozone in a foot bath and wash pen.

An ozone delivery method is disclosed that comprises providing ozonated water and applying said ozonated water to a surface to disinfect and dean said surface via said application of said ozonated water to said surface. The ozonated water comprises dissolving ozone gas in water at preferable concentrations of 0.04 parts per million to 1.2 parts per million. The method further comprises injecting said ozonated water through a hose and spraying said ozonated water out of said hose onto said surface. The surface can comprise at least one of the following: a calf milk bottle, a washing machine used to wash teat wiping towel an animal's exterior, an animal teat, an animal hoof, equipment, dairy equipment, a dairy surface, a floor surface, a dairy floor surface, an animal stall, a milking pit surface, and milking pit equipment. The method can further comprise providing a foot bath filled with said ozonated water wherein an animal enters said foot bath to disinfect said animal in said ozonated water and providing a wash pen utilizing said ozonated water wherein an animal enters said pen to disinfect said animal in said ozonated water. The method can comprise educting ozone into a drop hose and a pre-dip line at periodic intervals and educting ozone into a foot bath to provide refreshed ozonated water in said foot bath.

An ozone delivery system is further disclosed that comprises ozonated water and a surface for applying said ozonated water for disinfecting and cleaning said surface via said application of said ozonated water to said surface. The system can further comprise a programmable logic controller and a relay for computer-controlled automation for educting ozone into said ozonated water wherein said ozonated water comprises ozone dissolved at preferable concentrations of 0.04 parts per million to 1.2 parts per million. The system can further comprise said ozonated water injected through a hose and said ozonated water sprayed out of said hose onto said surface. The surface can comprise at least one of the following: a calf milk bottle, a washing machine used to wash teat wiping towel, an animal's exterior, an animal teat, an animal hoof, equipment, dairy equipment, a dairy surface, a floor surface, a dairy floor surface, an animal stall, a milking pit surface, and milking pit equipment. The system can further comprise a foot bath filled with said ozonated water wherein an animal enters said foot bath to disinfect said animal in said ozonated water and a wash pen utilizing said ozonated water wherein an animal enters said wash pen to disinfect said animal in said ozonated water. The system can additionally comprise ozone educted into a drop hose and a pre-dip line at periodic intervals and ozone educted into a foot bath to provide refreshed ozonated water in said foot bath.

An ozone delivery apparatus is disclosed that comprises ozonated water exiting a hose towards a surface wherein said surface is disinfected and cleaned via application of said ozonated water to said surface, a foot bath filled with said ozonated water wherein an animal enters said foot bath to disinfect said animal in said ozonated water, and a wash pen utilizing said ozonated water wherein an animal enters said pen to disinfect said animal in said ozonated water. The apparatus can further comprise ozone educted into a drop hose and a pre-dip line at periodic intervals and ozone educted into a foot bath to provide refreshed ozonated water in said foot bath. The surface can comprise at least one of the following: a calf milk bottle, a washing machine used to wash teat wiping towel, an animal's exterior, an animal teat, an animal hoof, equipment, dairy equipment, a dairy surface, a floor surface, a dairy floor surface, an animal stall, a milking pit surface, and milking pit equipment.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

The embodiments now will be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1A:
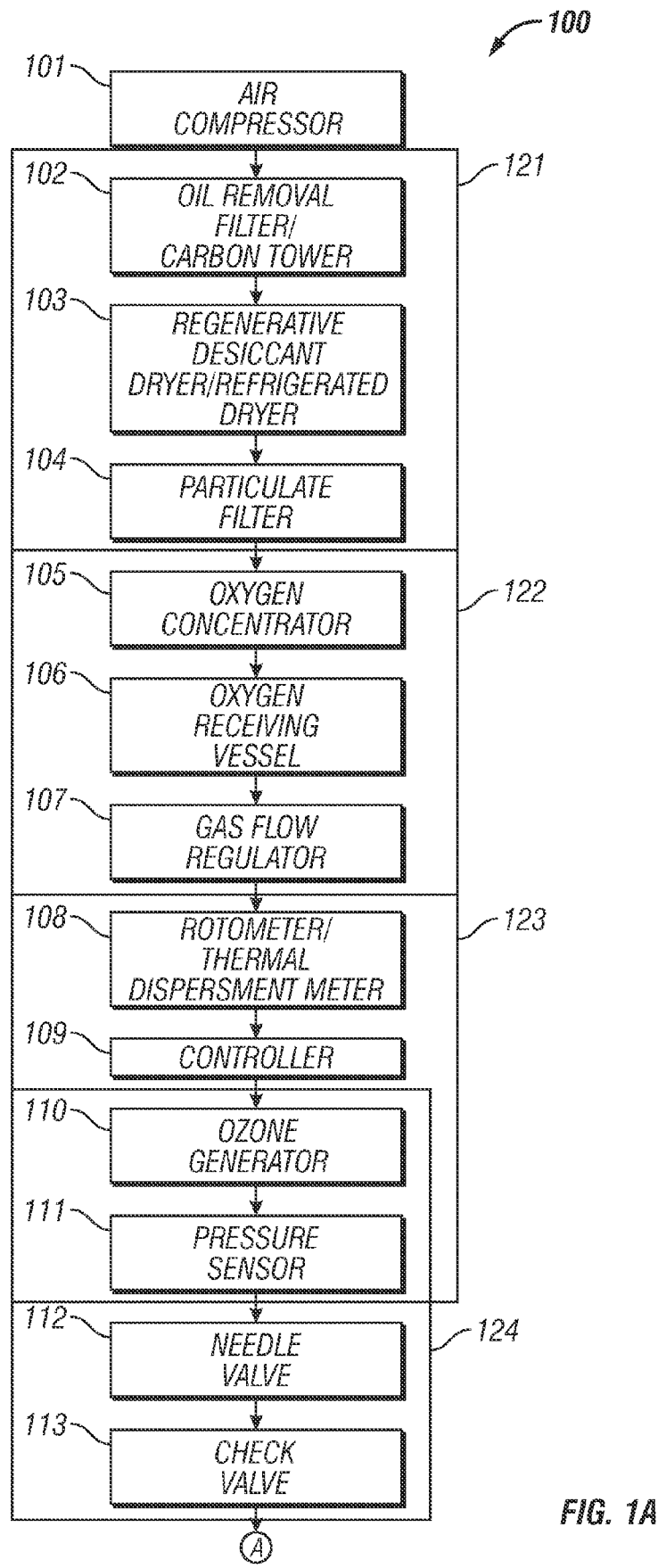
FIG. 1A illustrates a block diagram of an ozone delivery system and apparatus, in accordance with the disclosed embodiments.
Figure 1A:
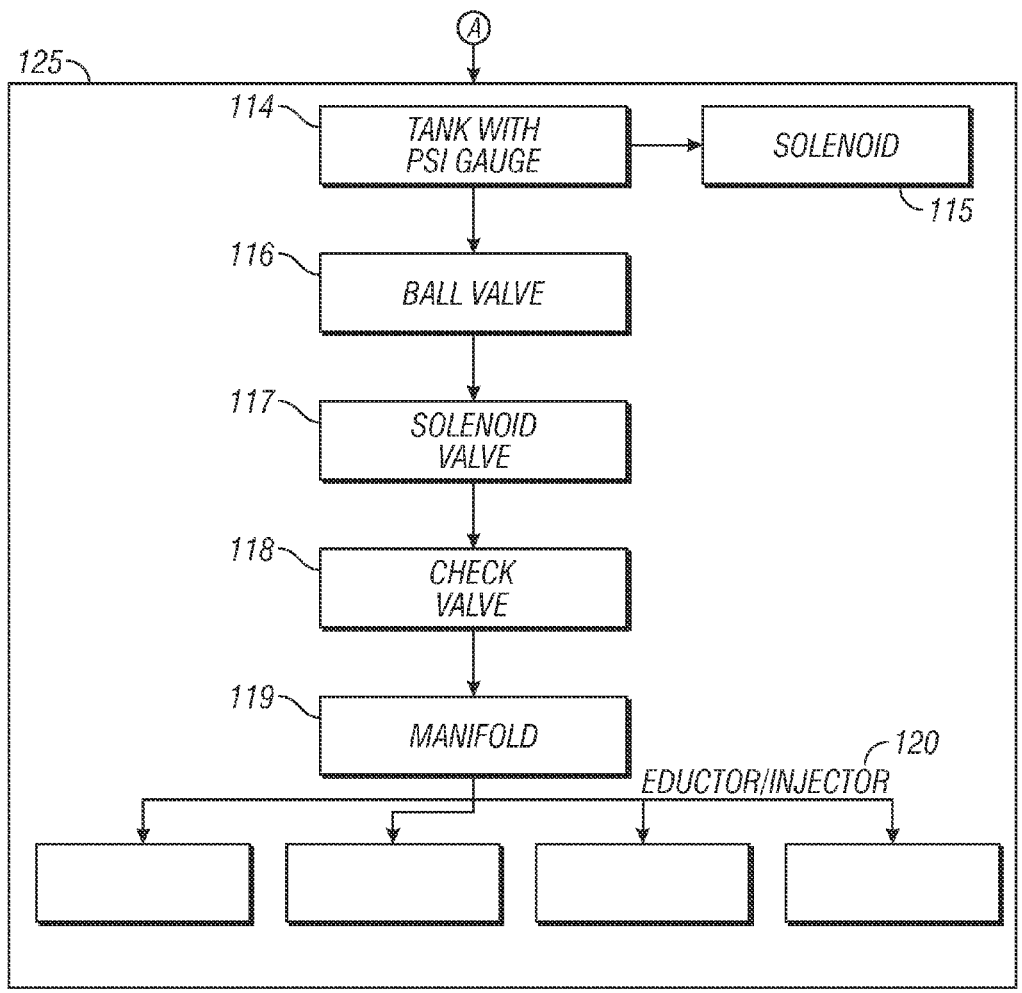

FIG. 1A illustrates a block diagram 100 of an ozone delivery system and apparatus, in accordance with the disclosed embodiments. The disclosed embodiments can include a system of a computer-controlled system for precise injected eduction through solenoid valves and/or automated valves 115, 117 to complement standard eduction processes. The ozone delivery system uses ozonated water in preferable concentration ranges from 0.04 ppm to 1.2 ppm (parts per million) depending on application, to safely disinfect animals and equipment, and reduce the need for harmful chemical disinfectants around a dairy, for example. Ozone is a powerful oxidizing agent. At appropriate usage levels, ozone is safe for humans and animals. The disclosed embodiments offset all expenses related to the purchase, storage, transportation, disposal and handling of disinfecting chemicals, e.g. insurance, facility space, chemical cost, etc. Because the system uses ozone, which degrades to oxygen, there is no environmental footprint to deal with, nor hazardous chemicals to drain into the water supply.

The ozone delivery system can include an air compressor 101 coupled to an oil removal filter/carbon tower 102. The oil removal filter/carbon tower 102 is further coupled to a regenerative desiccant dryer/refrigerated dryer 103 and a particulate filter 104. The oil removal filter/carbon tower 102, regenerative desiccant dryer/refrigerated dryer 103, and a particulate filter 104 can be contained or housed in a component 121. Next, an oxygen concentrator 105 is coupled to an oxygen receiving vessel 106 and a gas flow regulator 107. The oxygen concentrator 105, oxygen receiving vessel 106, and a gas flow regulator 107 can be contained or housed in a component 122. An optional rotometer/thermal dispersment meter 108 can be coupled to controller 109 in component or housing 123. Also in housing 123, the controller 109 is coupled to an ozone generator 110 and pressure sensor 111 as well as an ambient gas detector. The controller 109 may turn off the ozone generator 110 and/or close solenoid valves 115, 117 based on parameters set regarding pressure, ambient ozone levels, or any other preset parameters. The controller 109 is also connected to the automated valves which feed the footbaths and evacuate the footbaths with the valves being cycled based on timing, water flow or water level measurements. The pressure sensor 111 is coupled to a needle valve 112 and a check valve 113, housed in component 124. The check valve 113 is coupled to a tank with a pressure gauge 114 and with an associated solenoid 115. The tank with a pressure gauge 114 is coupled to a ball valve 116, solenoid valve 117, check valve 118, and manifold 119, all of which are housed in component 125. The manifold 119 is coupled to the eductor/injector 120 via a check valve and ball valve.

Figure 1B:
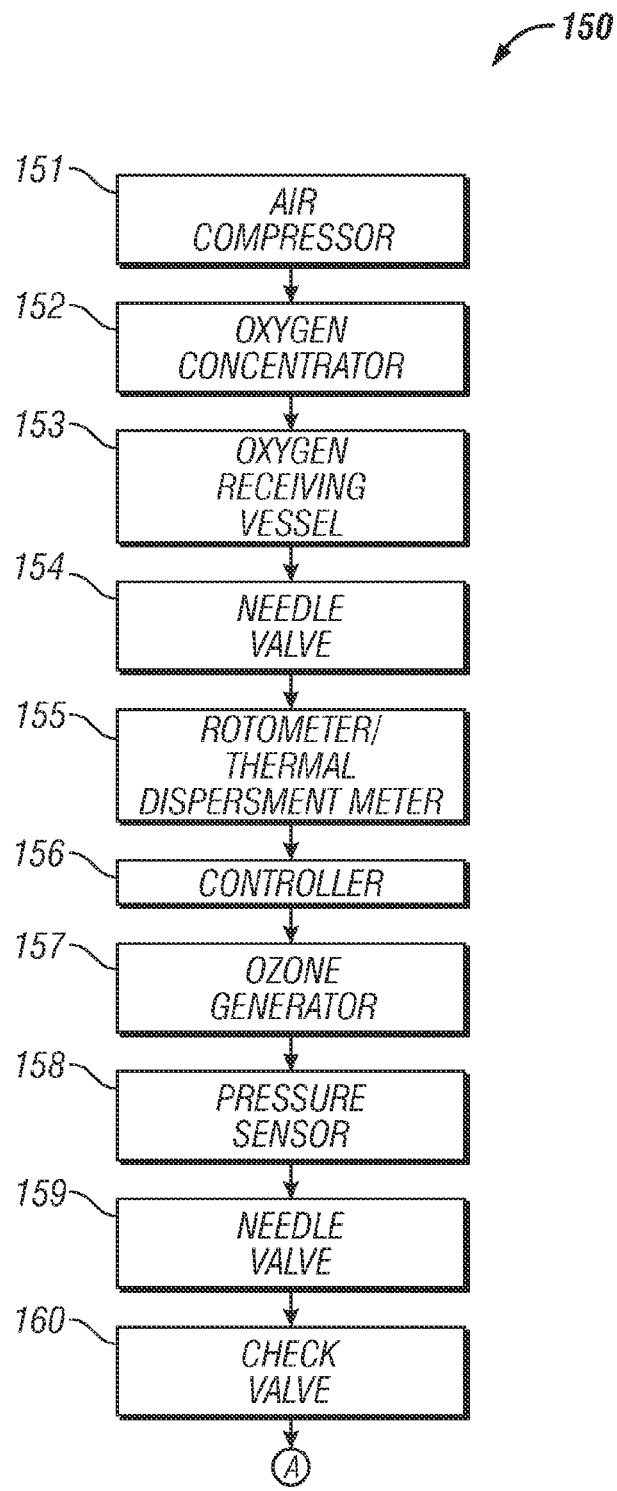
FIG. 1B illustrates a block diagram of an ozone delivery system and apparatus, in accordance with the disclosed embodiments.
Figure 1B:
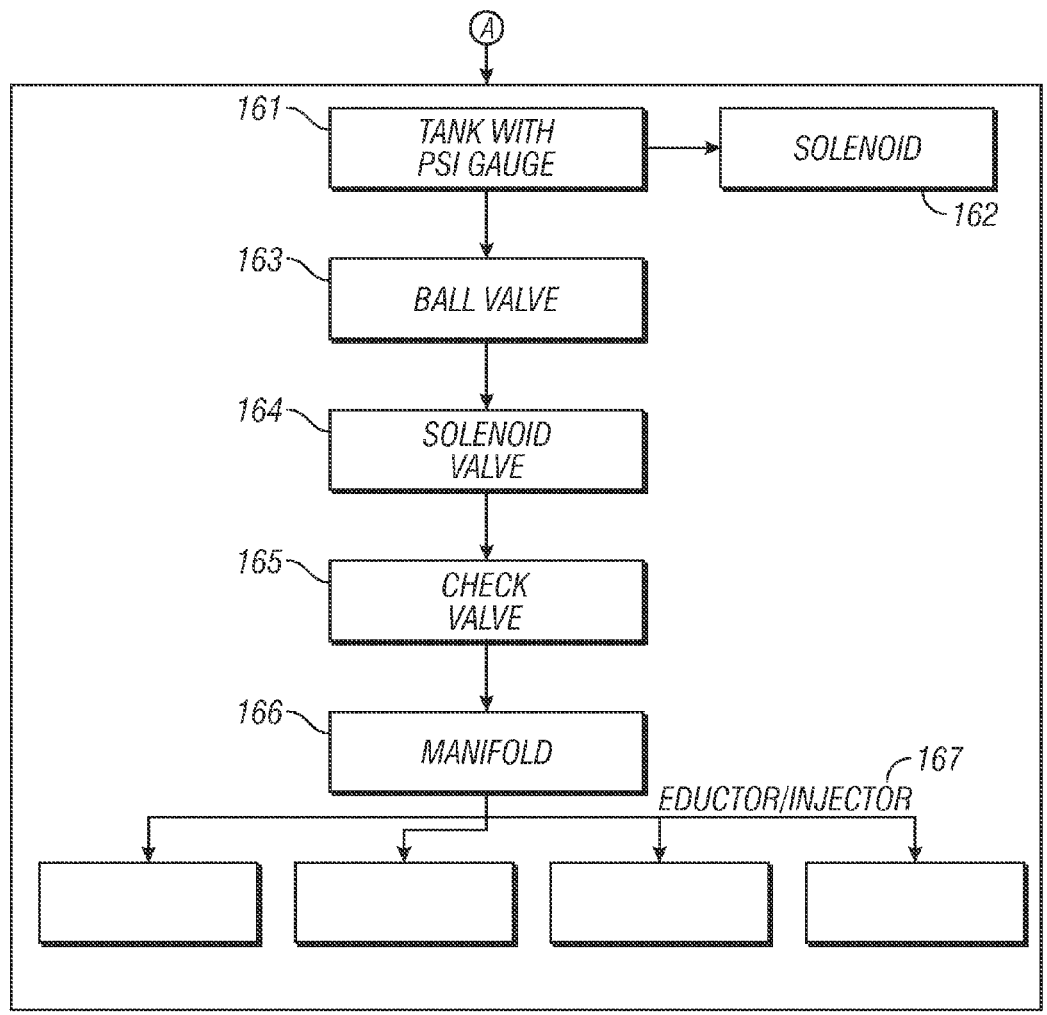

FIG. 1B illustrates a block diagram 150 of an ozone delivery system and apparatus, in accordance with the disclosed embodiments. The ozone delivery system can include an air compressor 151 coupled to an oxygen concentrator 152, an oxygen receiving vessel 153, and a needle valve 154. An optional rotometer/thermal dispersment meter 155 can be coupled to controller 156. The controller 156 is coupled to an ozone generator 157 and pressure sensor 158 as well as an ambient gas detector. The controller 156 may turn off the ozone generator 157 and/or close solenoid valves 162, 164 based on parameters set regarding pressure, ambient ozone levels, or any other preset parameters. The controller 156 is also connected to the automated valves which feed the footbaths and evacuate the footbaths with the valves being cycled based on timing, water flow or water level measurements. The pressure sensor 158 is coupled to a needle valve 159 and a check valve 160. The check valve 160 is coupled to a tank with a pressure gauge 161 and with an associated solenoid 162. The tank with a pressure gauge 161 is coupled to a ball valve 163, solenoid valve 164, check valve 165, and manifold 166. The manifold 166 is coupled to the eductor/injector 167 via a check valve and ball valve.

Figure 2:
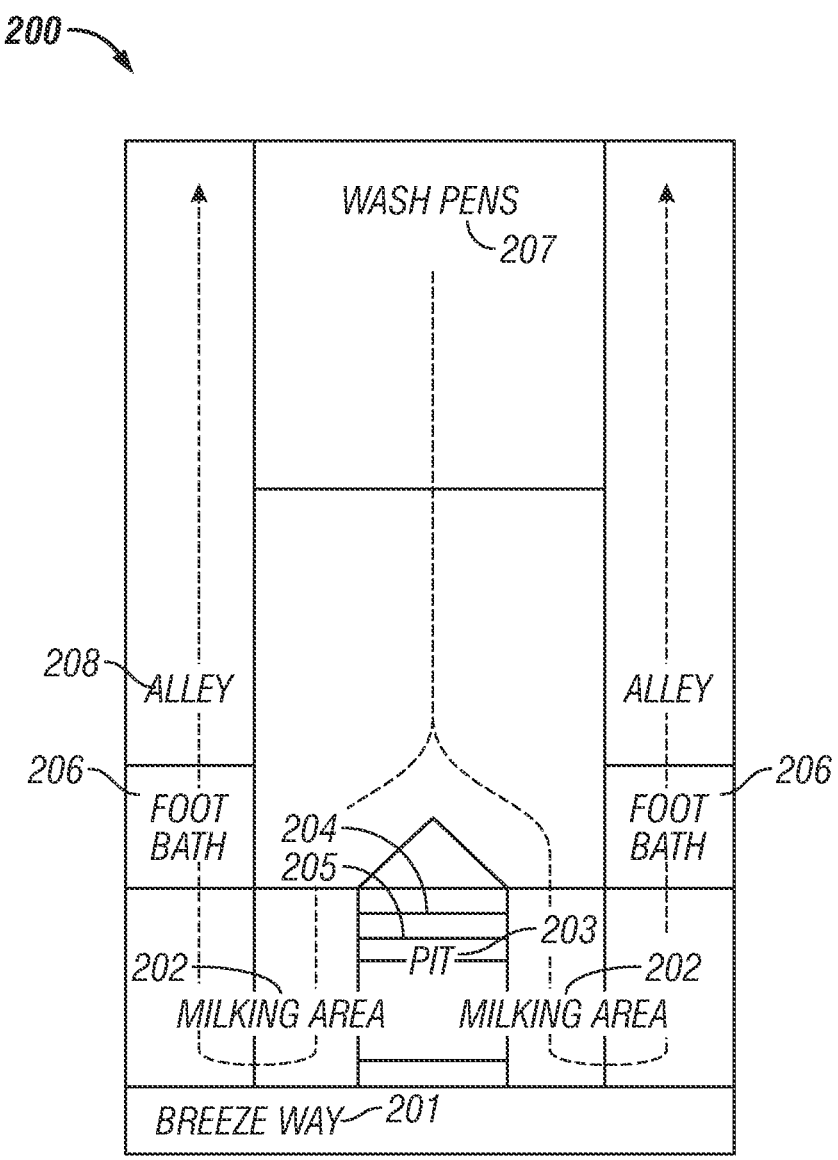
FIG. 2 illustrates a pictorial diagram of an exemplary dairy milking and disinfecting area, in accordance with the disclosed embodiments.

FIG. 2 illustrates a pictorial diagram 200 of an exemplary dairy milking and disinfecting area, in accordance with the disclosed embodiments. The disclosed ozone delivery system and method are designed to replace iodine pre-dip for teats and copper sulfate disinfectants. Both teats and hooves are disinfected and protected from disease through the use of wash-pen and sprayer injections, and/or other footbath products, filled with ozonated water. The ozone delivery system and method sterilizes all equipment and floor surfaces. Using ozonated water as a disinfectant does not damage the metal and/or plastic components of diary equipment. This system could potentially be used during the clean-in-place cleaning process.

An animal such as, for example, a cow can enter the wash pen 207 of a milking area 202. Ozonated water-filled drop hoses 205 spray ozone-saturated water to disinfect the equipment and floor surfaces in the pit. Animals and people surrounding the ozonated water-filled drop hoses do not risk exposure to a harmful mist of chemicals spraying from the drop hoses. The drop hoses closest to the breezeway 201 can optionally contain non-ozonated water for human consumption. Low pressure spray hoses 204 can be installed in the drop hose line 205 to spray teats with ozone-saturated water as a mastitis preventative pre-treatment. As the cow moves out of the milking area 202 the cow walks through an ozonated water-filled foot bath 206 to remove remaining fecal material and other soils from the hooves. The foot bath 206 can be equipped with an automatic drain to allow for quick draining of contaminated water and fecal material. The foot baths 206 can be periodically filled with ozone-saturated water. The footbath can be periodically filled with fresh ozonated water through a service line connected to the drop hose line 205 for eduction of fresh ozone into drop hose 205 and pre-dip lines at periodic intervals, while simultaneously "topping-off" foot baths 206 with fresh, educted ozone.

Figure 3:
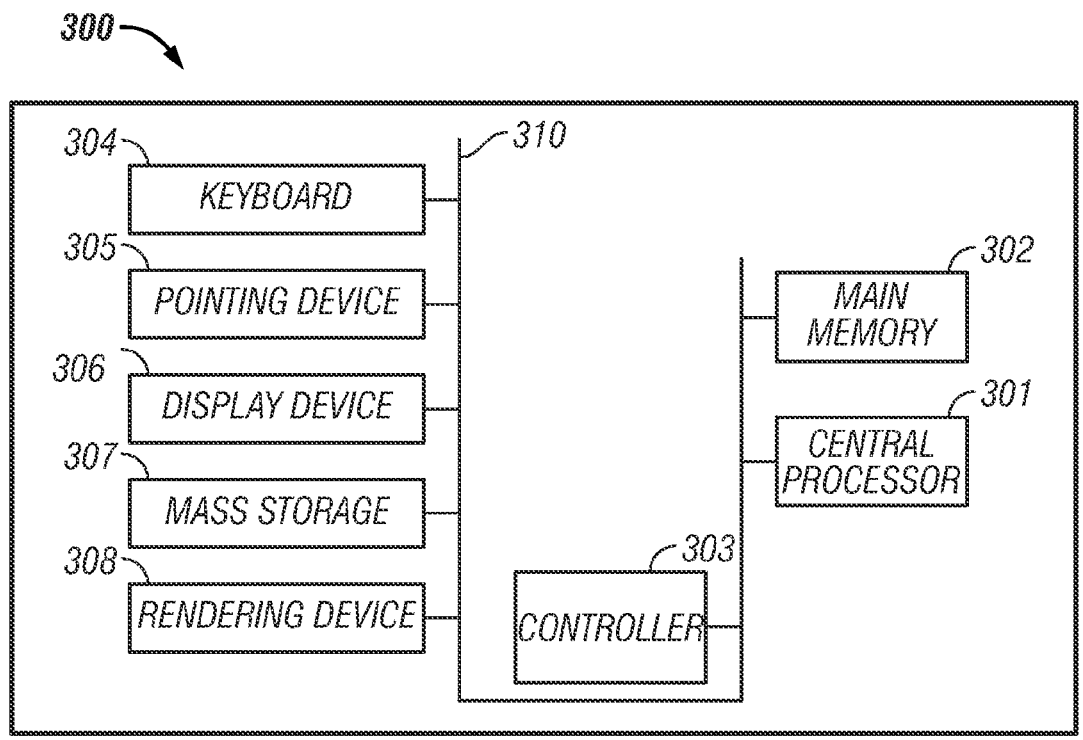
FIG. 3 illustrates a schematic view of a computer system in which the present invention may be embodied.
Figure 4:
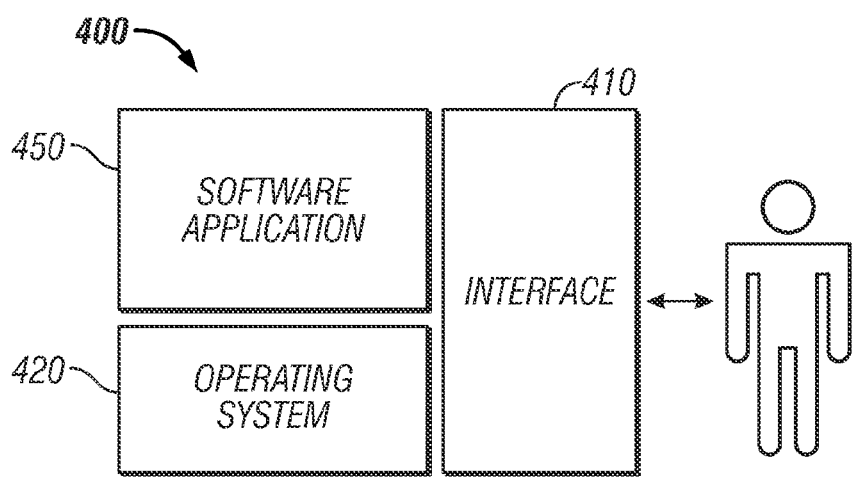
FIG. 4 illustrates a schematic view of a software system including an operating system, application software, and a user interface for carrying out the present invention.

FIGS. 3-4 are provided as exemplary diagrams of data processing environments in which embodiments of the present invention may be implemented. It should be appreciated that FIGS. 3-4 are only exemplary and are not intended to assert or imply any limitation with regard to the environments in which aspects or embodiments of the present invention may be implemented. Many modifications to the depicted environments may be made without departing from the spirit and scope of the present invention.

As depicted in FIG. 3, the present invention may be embodied in the context of a data-processing apparatus 300 comprising a central processor 301, a main memory 302, an input/output controller 303, a keyboard 304, a pointing device 305 (e.g., mouse, track ball, pen device, or the like), a display device 306, and a mass storage 307 (e.g., hard disk). Additional input/output devices, such as a rendering device 308, may be included in the data-processing apparatus 300 as desired. The rendering device 308 may be a standalone single function device such as a dedicated printer, scanner, copy machine, etc. Preferably, rendering device 308 functions as a multifunction device capable of multiple rendering functions such as printing, copying, scanning, faxing, etc. As illustrated, the various components of the data-processing apparatus 300 communicate through a system bus 310 or similar architecture. The disclosed embodiments can also be controlled via a programmable logic controller (i.e., PLC) and relays.

A computer software system 400 for directing the operation of the data-processing apparatus 300 is depicted in FIG. 4. Software application 450, which is stored in main memory 302 and on mass storage 307, can include a kernel or operating system 420 and a shell or interface 410. One or more application programs such as application software 450 may be "loaded" (i.e., transferred from mass storage 307 into the main memory 302) for execution by the data-processing apparatus 300. The data-processing apparatus 300 thus can receive user commands and data through user interface 410. These inputs may then be acted upon by the data-processing apparatus 300 in accordance with instructions from operating module 420 and/or application module 450.

The interface 410, which is preferably a graphical user interface (e.g., GUI) or human machine interface (e.g., HMI), also serves to graphically display cleaning and disinfecting records, ozonated water levels, maintain and monitor concentration of ozone in water, entry and exit gates controls, drainage system controls, etc., whereupon a user may supply additional inputs or terminate a particular session. In one particular embodiment, operating system 420 and interface 410 can be implemented in the context of a "Windows" system. Application module 450, on the other hand, can include instructions such as the various operations described herein with respect to the various components and modules described herein such as, for example, the method 200 depicted in FIG. 2. Computer controls are also used to maintain off gas levels within OSHA-permitted regulations to ensure worker safety.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A preventative treatment ozone delivery system installed at a dairy, comprising: ozonated water comprising ozone dissolved at concentrations of 0.04 parts per million to 1.2 parts per million, the ozone educted into a low-pressure hose and a pre-dip line with ozonated water;

an ozone delivery apparatus comprising: a programmable logic controller and a relay for computer-controlled automation for educting ozone into the ozonated water, wherein the programmable logic controller is coupled to an ozone generator, a pressure sensor, and an ambient gas detector, and wherein the programmable logic controller turns off the ozone generator or closes solenoid valves based on set parameters regarding pressure and ambient ozone level;

and a surface for applying the ozonated water for disinfecting and cleaning the surface through the application of the ozonated water to the surface through application with a low-pressure hose.

2. The system of claim 1, further comprising the ozonated water injected through a hose and the ozonated water sprayed out of the hose onto the surface.

3. The system of claim 1, wherein the surface comprises at least one of the following: a calf milk bottle, a washing machine used to wash teat wiping towels, an exterior part of an animal, equipment, a dairy surface, a floor surface, an animal stall, a milking pit surface, and milking pit equipment.

4. The system of claim 1, further comprising a foot bath filled with the ozonated water wherein an animal enters the foot bath to disinfect the animal in the ozonated water, wherein the foot bath comprises a service line that re-fills the foot bath with ozonated water.

5. The system of claim 1, further comprising a wash pen utilizing the ozonated water, wherein an animal enters the wash pen to disinfect the animal in the ozonated water, prevent dirt and bacteria from entering a milk supply, and prevent disease transmission between a plurality of animals.

6. The system of claim 1, further comprising ozone educted into a drop hose and the pre-dip line at periodic intervals, and the ozone educted into a foot bath to provide refreshed ozonated water in the foot bath.

7. A preventative treatment ozone delivery apparatus comprising: ozonated water comprising ozone dissolved at concentrations of 0.04 parts per million to 1.2 parts per million, the ozone educted into a low-pressure hose and a pre-dip line with ozonated water, the ozonated water exiting the low-pressure hose towards a surface, wherein the surface is disinfected and cleaned through application of the ozonated water to the surface;

and a programmable logic controller and a relay for computer-controlled automation for educting ozone into the ozonated water, wherein the programmable logic controller is coupled to an ozone generator, a pressure sensor, and an ambient gas detector, and wherein the programmable logic controller turns off the ozone generator or closes solenoid valves based on set parameters regarding pressure and ambient ozone level.

8. The apparatus of claim 7, further comprising a foot bath filled with the ozonated water wherein an animal enters the foot bath to disinfect the animal in the ozonated water, wherein the foot bath comprises a service line that re-fills the foot bath with ozonated water; and a wash pen utilizing the ozonated water wherein the animal enters the pen to disinfect the animal in the ozonated water.

9. The apparatus of claim 7, further comprising ozone educted into a drop hose and the pre-dip line at periodic intervals and ozone educted into a foot bath to provide refreshed ozonated water in the foot bath.

10. The apparatus of claim 7, wherein the surface comprises at least one of the following: a calf milk bottle, a washing machine used to wash teat wiping towels, an exterior part of an animal, equipment, a dairy surface, a floor surface, an animal stall, a milking pit surface, and milking pit equipment.

11. A preventative treatment ozone delivery apparatus, comprising: ozonated water comprising ozone dissolved at concentrations of 0.04 parts per million to 1.2 parts per million the ozone educted into a low-pressure hose and a pre-dip line with ozonated water, the ozonated water exiting the low-pressure hose towards a surface wherein the surface is disinfected and cleaned through application of the ozonated water to the surface;

a programmable logic controller and a relay for computer-controlled automation for educting ozone into the ozonated water, wherein the programmable logic controller is coupled to an ozone generator, a pressure sensor, an ambient gas detector, and automated valves that feed and evacuate a foot bath, wherein the automated valves are cycled based on timing, water flow, or water level measurements, and wherein the programmable logic controller turns off the ozone generator or closes solenoid valves based on set parameters regarding pressure and ambient ozone level;

and a foot bath filled with water, wherein the ozone is educted into the foot bath, wherein an animal enters said foot bath to disinfect the animal in the ozonated water, and wherein the foot bath comprises a service line that re-fills said foot bath with ozonated water.

12. The apparatus of claim 11, further comprising a wash pen utilizing the ozonated water wherein an animal enters the pen to disinfect the animal in the ozonated water.

13. The apparatus of claim 11, further comprising ozone educted into a drop hose and the pre-dip line at periodic intervals and ozone educted into a foot bath to provide refreshed ozonated water in the foot bath.

14. The apparatus of claim 11, wherein the surface comprises at least one of the following: a calf milk bottle, a washing machine used to wash teat wiping towels, an exterior part of an animal, equipment, a dairy surface, a floor surface, an animal stall, a milking pit surface, and milking pit equipment.

15. The system of claim 1, wherein the ozone generator generates the ozonated water without mixing or storing the ozonated water in a reservoir.

16. The system of claim 1, further comprising an air compressor coupled to an oil removal filter.

17. The system of claim 1, further comprising a regenerative dessicant dryer and a particulate filter coupled to an oil removal filter.

18. The system of claim 1, further comprising an oxygen concentrator coupled to an oxygen receiving vessel and a gas flow regulator.

19. The system of claim 1, further comprising a needle valve and a first check valve coupled to the pressure sensor, wherein the first check valve is further coupled to a tank with a pressure gauge and a first solenoid valve, and wherein the tank with the pressure gauge is coupled to a ball valve, a second solenoid valve, a second check valve, and a manifold, wherein the manifold is coupled to an eductor.

20. The system of claim 1, further comprising a housing component housing the programmable logic controller, an air compressor, an oil removal filter, a regenerative dessicant dryer, a particulate filter, an oxygen concentrator, an oxygen receiving vessel, a gas flow regulator, a needle valve, a check valve, said pressure sensor, a first check valve, a tank, a pressure gauge, a first solenoid valve, a ball valve, a second solenoid valve, a second check valve, and a manifold.

* * * * *